United States Patent [19]

Yang

[11] Patent Number: 5,030,229
[45] Date of Patent: Jul. 9, 1991

[54] DISPOSABLE URINARY PAD

[75] Inventor: Ching-Yun M. Yang, Princeton Junction, N.J.

[73] Assignee: Chicopee, New Brunswick, N.J.

[21] Appl. No.: 464,487

[22] Filed: Jan. 12, 1990

[51] Int. Cl.$^5$ ............................................. A61F 13/16
[52] U.S. Cl. ................................. 604/385.1; 604/378; 604/370; 604/369
[58] Field of Search ............... 606/368, 378, 369, 370, 606/379, 384

[56] References Cited

U.S. PATENT DOCUMENTS

| | | | |
|---|---|---|---|
| 4,568,341 | 2/1986 | Mitchell et al. | 604/368 |
| 4,605,402 | 8/1986 | Iskra | 604/368 |
| 4,681,577 | 7/1987 | Stern et al. | 604/378 |
| 4,685,914 | 8/1987 | Holtman | 604/368 |
| 4,755,421 | 7/1988 | Manning et al. | 428/224 |
| 4,865,596 | 9/1989 | Weisman et al. | 604/368 |

*Primary Examiner*—Stephen C. Pellegrino
*Assistant Examiner*—Gary Jackson
*Attorney, Agent, or Firm*—Jason Lipow

[57] ABSTRACT

This invention provides a disposable urinary pad comprising a liquid-impermeable backing, an absorbent core and a liquid permeable facing adhered to the shell so as to entrap the absorbent core therebetween. The absorbent core comprises a web of absorbent fibers and superabsorbent material and has a liquid-permeable transfer layer adjacent to one surface. The absorbent core is pleated, as in an M-configuration, to form therein a center lengthwise channel. The transfer layer, after pleating of the absorbent core, extends down the sides of the core so as to provide a liquid path to the bottom of the core.

17 Claims, 3 Drawing Sheets

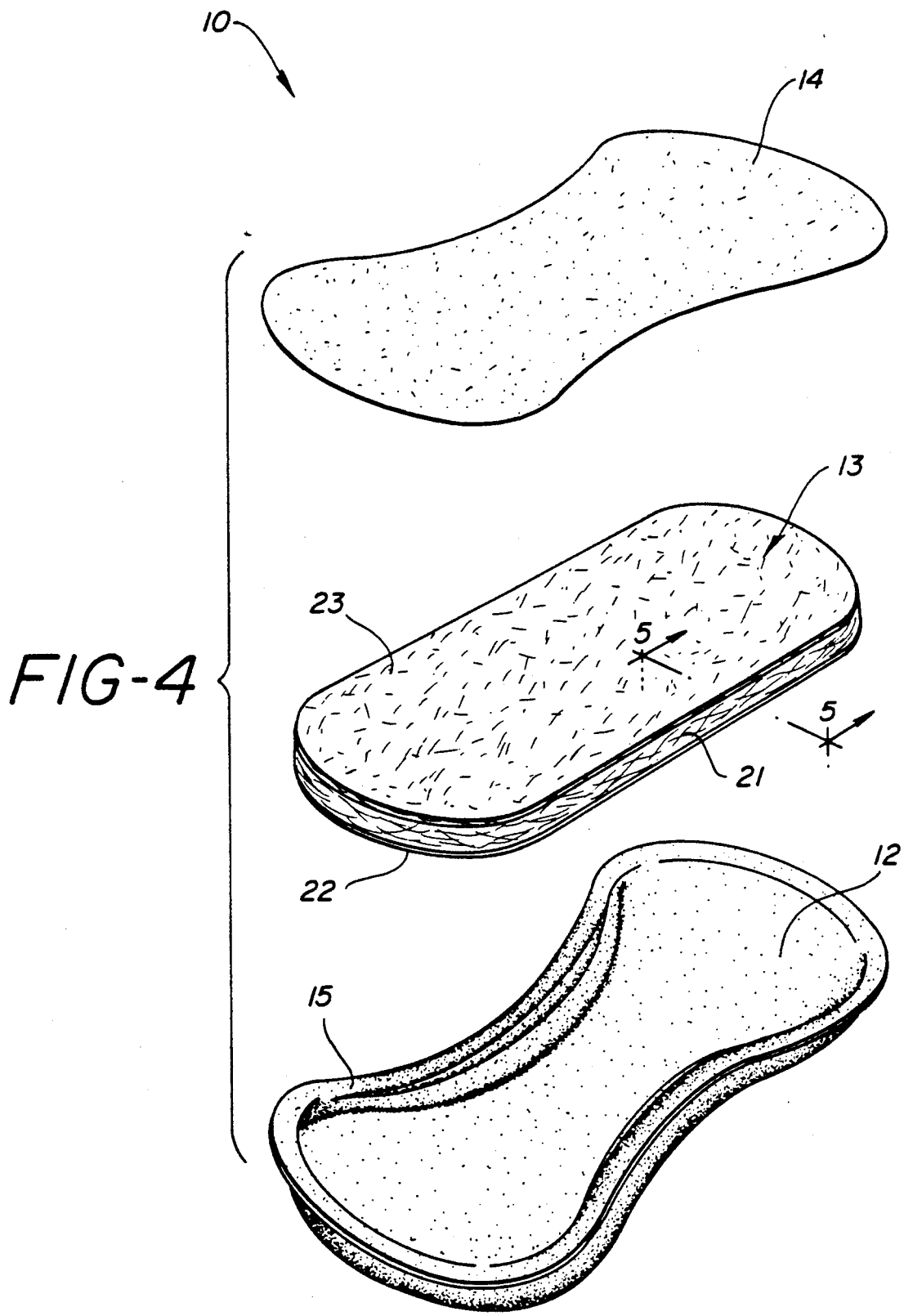

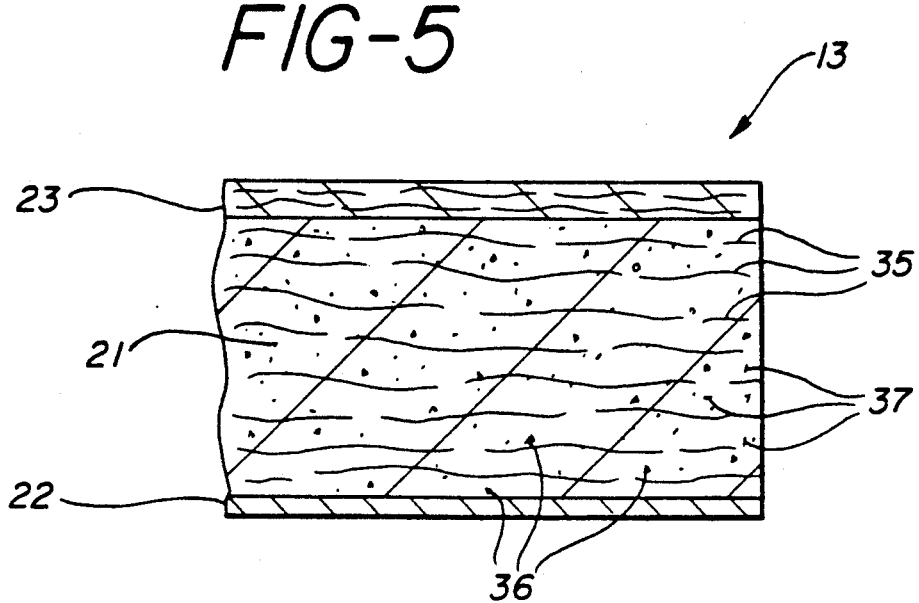
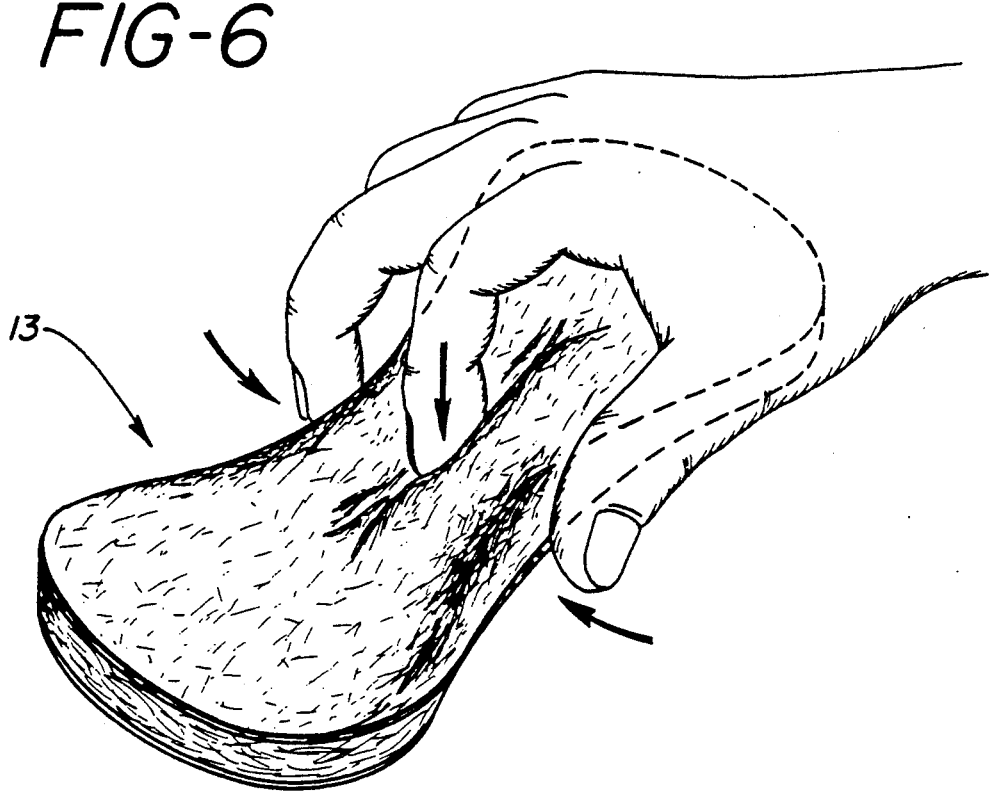

DISPOSABLE URINARY PAD

BACKGROUND OF THE INVENTION

The present invention relates to a new and improved disposable urinary pad having high liquid impact capacity, high liquid retention, and which allows the skin of the wearer to remain dry.

Disposable absorbent products have been known for some time, including such products as disposable diapers, sanitary napkins, wound dressings, bandages, incontinent pads, and the like. These products incorporate an absorbent batt which is used to absorb and hold or contain body fluids. Initially in many of these products, especially diapers and sanitary napkins, the absorbent batt comprised what is termed "wadding" or plies of tissue. The wadding was disposed between a liquid-impermeable backing and a liquid-permeable facing and the plies of tissue were used to absorb and, hopefully, contain the liquid within the product. A diaper which utilizes such an absorbent batt is disclosed in U.S. Reissue Pat. No. 26,151.

The wadding type of product was replaced, for the most part, by an improved absorbent batt which comprises what is termed "fluffed wood pulp fibers". This absorbent batt comprises a layer of individualized wood pulp fibers with the layer having substantial thickness. A diaper which incorporates such fluffed wood pulp absorbent batt is described in U.S. Pat. No. 2,788,003. This diaper had improved absorbent capacity and somewhat better containment than a diaper using a wadding layer. Also, the fluffed wood pulp layer is quite soft, flexible, and conformable, and, hence, produces an improved diaper over diapers using wadding as the absorbent layer.

Although fluffed wood pulp absorbent batts have a good absorptive capacity, the efficiency with which the capacity is used in a diaper or sanitary napkin is poor. The reason for this is that the fluid to be absorbed is generally deposited in a localized area within the absorbent batt, and the ability of the fluid to move along the plane of the batt is poor. The fluid tends to follow a radial wicking path and consequently moves to the closest edge of the batt where it generally is no longer contained and the product leaks.

In designing a disposable urinary device, one must be mindful of the special problems of an incontinent adult. First, the void of an adult generally is much higher in volume than that of an infant, so a device with greater absorptive capacity than that of an infant's diaper is needed. Second, a bulge under clothing is accepted by society for an infant, but the ambulatory adult with an incontinence problem longs for a product which is not visible through ordinary clothing. Third, the proportions and shape of the legs and torso of the adult differ considerably from those of an infant. Therefore, a mere enlargement of an infant diaper is not a satisfactory product.

A number of years ago, "superabsorbent materials", i.e., materials which will absorb many times their weight of liquid, were developed. Since the development of such materials, attempts to incorporate them in absorbent products such as diapers to enhance the absorption performance of these products have been made. Theoretically, a minimum amount of superabsorbent incorporated in a product would make that product perform as well or better than the prior art products. Perhaps one of the first products to incorporate such a superabsorbent material in a disposable diaper is disclosed in U.S. Pat. No. 3,670,731. This patent discloses an absorbent dressing comprising an absorbent layer sandwiched between a permeable facing and an impermeable backing sheet. The absorbent layer contains water-insoluble cross-linked hydrocolloid polymer as the superabsorbent material.

U.S. Pat. No. 3,525,337 discloses an absorbent element for sanitary napkins or the like consisting of an accordion-pleated pad formed from a thin layer of absorbent fibers faced on each side with sheets of absorbent cellulose wadding. The pleats are secured in their folded configuration by having the peaks of the folds on one side of the pad attached to an anchoring sheet.

U.S. Pat. No. 4,685,914 discloses a disposable urinary pad which utilizes superabsorbent material. The pad disclosed in this patent comprises a liquid-impermeable, substantially flexible shell containing a superstructure consisting essentially of a fibrous web of hydrophobic, wet resilient, dry resilient fibers and an absorbent medium in intimate contact with at least a portion of said superstructure and at least a portion of said shell. In a preferred embodiment, the superstructure is a corrugated fibrous web, e.g., of polyester fibers, and the absorbent medium is a superabsorbent material.

U.S. Pat. No. 4,501,586 discloses an absorbent structure comprising a moisture-impermeable backing, an absorbent batt and a moisture-permeable cover covering at least the side opposite the moisture-impermeable backing. The absorbent batt is of loosely-compacted, cellulosic fibers and is provided with a reservoir having a capacity of at least 10 cc. The reservoir is formed by compression of the fibers in the reservoir zone and is located so that the product, when worn, retains the proper shape.

U.S. Pat. No. 4,731,070 discloses an absorbent article particularly suitable for use by male and female incontinents. The absorbent article includes a urine receptacle pocket offset to one end of the product and formed by folding the product and adhering together portions of a moisture impervious sheet that are folded over side marginal edges of an absorbent batt.

The present invention provides a new and improved absorbent product which possesses a large liquid storage capacity, which is conformable to the body of the wearer and comfortable in use, which is not readily apparent through normal clothing and which more efficiently utilizes the liquid-retentive capacity of the absorbent materials.

SUMMARY OF THE INVENTION

The present invention relates to a disposable urinary pad which comprises a liquid-impermeable backing, an absorbent core and a liquid-permeable facing adhered to said liquid-impermeable backing, so as to enclose the absorbent core therein.

The liquid-impermeable backing element may comprise a liquid-impermeable plastic film such as a polyethylene film. Preferably, however, the liquid-impermeable backing comprises a liquid-impermeable, soft, resilient cup-like shell having an outwardly extending peripheral flange. Such a shell may be formed from a sheet of blown polyethylene foam which is converted to the desired cup-like shape by a thermal molding process.

The absorbent core of the urinary pad comprises a liquid absorbent medium and a transfer layer. The function of the liquid absorbent medium is to absorb and retain liquid, e.g. urine, discharged into the urinary pad. The function of the transfer layer is to transfer discharged liquid to the absorbent medium and the lower regions of the urinary pad. Preferably, though not necessarily, the absorbent core comprises a layer of tissue which is disposed adjacent the lower surface thereof. The transfer layer is disposed adjacent the upper surface of the liquid absorbent medium to thereby form the absorbent core. The absorbent core is folded into an M-configuration prior to its insertion into the aforementioned molded liquid-impermeable shell. The transfer layer comprises a fibrous web having high loft and resiliency and substantially no resistance to liquid flow. The transfer layer preferably comprises a web of polyester fibers bonded with a resin binder.

The liquid-permeable facing may be apertured plastic film but is preferably a liquid permeable nonwoven fabric comprising hydrophobic fibers. The preferred hydrophobic fibers are bicomponent fibers having a polyester core and a polyethylene sheet, said fibers being fusion bonded by the application thereto of hot air.

In assembling the urinary pad, the absorbent core is folded into its M-fold configuration and inserted, with its transfer layer facing upwardly, into the liquid impermeable shell. The facing sheet is placed over the shell and secured to its outwardly extending peripheral flange, thereby enclosing the absorbent core in the shell.

The absorbent medium comprising the absorbent core includes a web of hydrophobic, wet resilient, dry resilient fibers and superabsorbent material. The fibers preferably comprise both wood pulp fibers and non-cellulosic synthetic fibers. Generally speaking, the wood pulp and synthetic fibers would be present in a ratio of about 50 to 95 weight percent wood pulp and about 50 to 5 weight percent non-cellulosic synthetic fibers. The amount of superabsorbent material included in the absorbent medium ranges from about 10 to 50 weight percent of the combined weight of the wood pulp fibers and the non-cellulosic synthetic fibers.

As a result of providing the absorbent core with the aforementioned M-fold configuration, the transfer layer extends down over the sides of the underlying absorbent medium so as to provide a liquid path to the bottom of the urinary pad.

The product of this invention has a high impact capacity, i.e. the product accepts a relatively large quantity of liquid quickly and retains it. Furthermore, the product does not leak or spill over. In other words, once the urine enters the pad, the urine remains entrapped within the product. The product also has a high liquid-holding capacity. In addition, the product maintains its surface dry thereby keeping any moisture away from the skin of the wearer. Still further, the product of this invention permits air circulation in the region where the product is worn which results in a high degree of comfort.

BRIEF DESCRIPTION OF THE DRAWINGS

FIG. 4 is an exploded view of the structural components of the urinary pad of FIG. 1, with the absorbent core thereof shown in its unfolded state.

FIG. 5 is a cross-sectional view taken along line 5—5 of FIG. 4.

FIG. 6 is a perspective view showing how the absorbent core of the urinary pad can be manually compressed in a lateral direction prior to its insertion into the liquid-impermeable core of the pad.

DETAILED DESCRIPTION OF THE INVENTION

Figure 1:
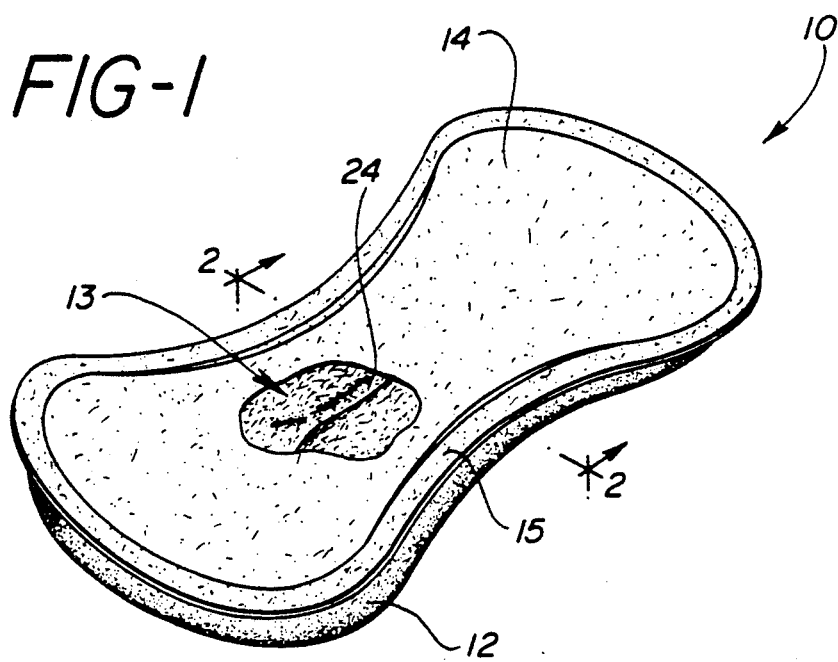
FIG. 1 is a perspective view of a disposable absorbent urinary pad of this invention.

FIG. 1 shows a disposable absorbent urinary pad 10 in accordance with the present invention. Pad 10 comprises a liquid-impermeable backing in the form of a cup-like foam shell 12 which has been preformed by a thermal molding process known in the art. Pad 10 also comprises an absorbent core 13, which is folded into an M-configuration and inserted into the shell 12. Pad 10 further comprises a liquid-permeable facing sheet 14 which is sealed to flange 15 of shell 12 and serves to enclose absorbent core 13 therein. Facing 14 is a liquid-permeable, generally hydrophobic fibrous web having a basis weight of 0.5 oz/yd$^2$. The three elements, i.e. shell 12, absorbent core 13, and facing 14, are assembled as shown in the drawings, to provide the disposable urinary pad.

Figure 2:
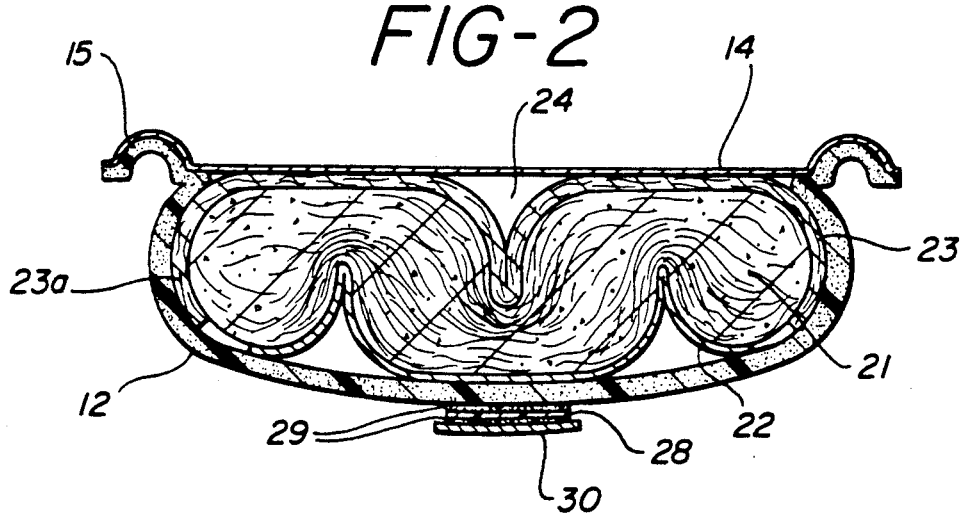
FIG. 2 is a cross-sectional taken along line 2—2 of FIG. 1.

FIG. 2 is a cross-sectional view of pad 10 of FIG. 1. Absorbent medium 21, comprising wood pulp fibers, synthetic fibers and a superabsorbent material, is optionally laid onto a layer of tissue 22. Transfer layer 23 is placed on the upper surface of the absorbent medium to complete the structure of absorbent core 13. The absorbent core is then formed into its M-configuration, thereby creating a channel 24 in the center of the pad. Channel 24 extends in the lengthwise direction of the pad and serves to receive discharged liquid and direct it toward the lower regions of the absorbent core.

Figure 3:
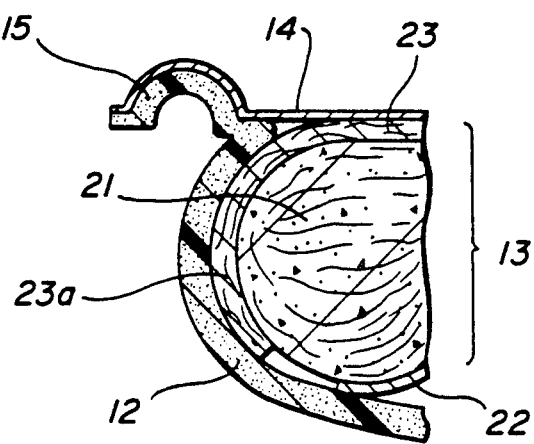
FIG. 3 is an enlarged view of the left-hand side of FIG. 2.

As can be seen more readily in FIG. 3, transfer layer 23 is configured after the M-folding so that its longitudinal side portions 23a extend downwardly over the longitudinal sides of absorbent medium 21 to provide a liquid path to the bottom regions of absorbent core 13 and liquid impermeable foam shell 12. The M-fold configuration is also advantageous in that it provides lateral compression recovery. Foam shell 12 has upper outwardly extending flanges 15 to which are adhered a liquid permeable nonwoven facing 14. There are adhesive means on the bottom of foam shell 12 to facilitate adhering the pad to the wearer's undergarment. The adhesive means comprise a tape 28 both faces of which are coated with pressure sensitive adhesive 29. The adhesive means are protected prior to use by removable cover sheet 30.

FIG. 4 shows urinary pad 10 of this invention with the structural elements thereof separated one from the other.

FIG. 5 is a partial, enlarged cross-sectional view of absorbent core 13 used in the present invention, prior to Pleating, and showing the spatial relationship of absorbent medium 21, tissue layer 22 and transfer layer 23. Absorbent medium 21 comprises a blend of wood pulp fibers 35, Pulpex ® material 36 and superabsorbent material 37. Pulpex ® is a thermoplastic synthetic polyolefin wood pulp fiber supplied by Hercules, Wilmington, Delaware, USA. Absorbent medium 21 resists wet collapse and consequently is able to maintain its void volume even after being wetted. The wet collapse resistance of absorbent medium 21 is provided by the presence of the Pulpex ® material which is hydrophobic and wet-resilient. The wood pulp fibers comprising absorbent medium 21 can be replaced in whole or part by other well-known liquid absorbent fibers, e.g. rayon fibers, cotton linters and the like. Staple length, heat fusible fibers, e.g. polyester fibers, polyolefin fibers or bicomponent fibers, may be substituted for the Pulpex ® material. The superabsorbent materials 37 comprising absorbent medium 21 may be selected from those commonly available and well-known to those skilled in the art. The superabsorbent material preferred for use in the present invention is poly-(sodium acrylate).

FIG. 6 illustrates a method for imparting the M-fold configuration to the absorbent core 13. Using a three-finger device, the center finger remains static while the two outside fingers move toward the center stationary finger, thus providing the M-fold and a reduction of the core width in its center portion. Generally, core 13 is squeezed, as shown, at its center and then placed into the liquid-impermeable foam shell 12 which holds it in it M-folded configuration. The M-fold configuration does not have to be restricted to the center of the core but could be extended throughout the entire product length if desired.

Turning now to a more detailed description of the components of the urinary pad of this invention, the hydrophilic fibers from which the absorbent core is made contains wood pulp fibers. Wood pulp is highly wettable, but collapses when wet. Non-cellulosic synthetic fibers such as but not limited to polyolefin fibers (polyethylene, polypropylene, and bicomponent fibers) are resistant to wet collapse because of their hydrophobicity. Thus, it has been found that by blending the wood pulp fibers with the aforementioned Pulpex ® material, an absorbent medium 21 with an optimum absorbency and good wet resilience can be obtained. Blending about 5 to 50 weight %, preferably about 20-25 weight %, of a non-cellulosic synthetic heat fusible material like Pulpex ® with the wood pulp fibers leads to a blended material with markedly improved wet collapse properties compared to 100% wood pulp, but which substantially retains the liquid absorbing properties of the wood pulp. In the preferred embodiment of this invention, the weight ratio of wood pulp fibers to the Pulpex ® synthetic polyethylene wood pulp is 77:23. It will be recognized that the ratio may be varied, if so desired.

The superabsorbent comprising the absorbent core is generally a water-insoluble, water-swellable polymeric substance capable of absorbing water in an amount which is at least 10 times the weight of the substance in its dry form. The superabsorbent may be in the form of powders, fibers, spheres, particles, bits of film, globules, or the like.

One type of superabsorbent material provides particles or fibers which may be described chemically as having a backbone of natural or synthetic polymers with hydrophilic groups or polymers containing hydrophilic groups being chemically bonded to the backbone or an intimate mixture therewith. Included in this class of materials are such modified natural and regenerated polymers as polysaccharides including, for example, cellulose and starch and regenerated cellulose which are modified by being carboxylalkylated, phosphonoalkylated, sulfoalkylated, or phosphorylated to render them highly hydrophilic. Such modified polymers may be cross-linked to improve their water-insolubility.

These same polysaccharides may also serve, for example, as the backbone on to which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophilic chain of the general formula

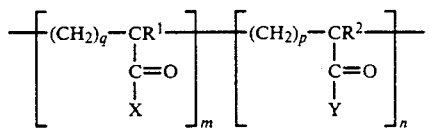

wherein $R^1$ and $R^2$ are selected from the group consisting of hydrogen and alkyl having 1 to 4 carbon atoms, X and Y are selected from the group consisting of —OH, —O(alkali metal), and —NH$_2$, wherein m is an integer having a value of 0 to about 5000, n is an integer having a value of 0 to about 5000, m plus n is at least 500, p is an integer having a value of 0 or 1, and q is an integer having a value of 1 to 4.

In addition to the modified natural and regenerated polymers, the hydrocolloid component may comprise wholly synthetic hydrophilic particles. Examples of those now known in the art are polyacrylonitrile fibers which may be modified by grafting moieties thereon such as polyvinylalcohol chains, polyvinyl alcohol itself, hydrophilic polyurethane, poly(alkyl phosphonates), partially hydrolyzed polyacrylamides (e.g., poly(N-N-dimethylacrylamide), sulfonated polystyrene, or a class of poly(alkyleneoxide). These highly hydrophilic synthetic polymers may be modified by other chemical treatments such as cross-linking or hydrolysis. Further examples known in the art are the non-ionic polymers such as polyoxyethylene, polyoxypropylene, and mixtures thereof which have been suitably crosslinked, either chemically or by irradiation. Still another more recent type is a derivative of isobutylene-maleic anhydride copolymer.

The absorbent medium 21 generally comprises about 10 to 50 weight %, based on its total weight, of superabsorbent material. In the preferred embodiment of this invention, the superabsorbent is poly-(sodium acrylate) and the superabsorbent comprises about 33 weight % of the total weight of the composite web. The balance of the composite web is a blend of wood pulp and Pulpex ® in a weight ratio of 77:23.

The absorbent medium 21 of wood pulp/noncellulosic synthetic fiber/superabsorbent can be prepared by methods well known in the art. For example, absorbent medium can be prepared by utilizing a ductless webber as disclosed in U.S. patent application Ser. No. 75,708, filed July 20, 1987, the disclosure of which is incorporated herein by reference. A single feed of a combined pulp/synthetic thermoplastic material may be fed to the webber, ground so as to individualize the same and then fed into an air stream into which superabsorbent material is also introduced. The combined pulp/synthetic thermoplastic material/superabsorbent may be collected and thermally bonded together to produce a stable web. Desirably, this web comprises a homogeneous blend of the three materials; however, there may be some settling of superabsorbent particles to the bottom of the web during subsequent processing steps.

Absorbent medium 21 is covered on at least its upper surface with a liquid-permeable transfer layer 23. The transfer layer, which has high loft and resiliency and substantially no resistance to liquid flow, comprises a web of polyester fibers having a denier of 6 and a length of 1½ inches. The web of polyester fibers is resin-bonded in known fashion, with the resin binder comprising 20% by weight of the total weight of polyester fibers and binder. The resin bonded polyester fiber fabric has a density of about 0.02 g/cm$^3$. The transfer layer may be a discrete layer of nonwoven fabric such as just described or may be formed in-situ by applying fiber and resin to one surface of the absorbent medium.

In the preferred embodiment, the liquid-impermeable backing is a substantially flexible polyethylene-containing foam shell which is preformed by a thermal molding process known in the art. The shell generally has a boat-like shape and ranges in thickness from about 1/64 to ¼ inch, preferably about 1/16 inch, in thickness. Shell 12 generally has a length which ranges from about 4 inches to about 12 inches, a width measured at its reduced center portion from about 2 inches to about 7 inches, and a depth of from about 0.5 to about 2.5 inches. The shell is resilient and, when deformed, substantially returns to its original shape.

The ethylene-containing polymer foam shell is prepared by known thermal molding processing. One preferred formulation for forming the ethylene-containing polymer foam material is identified as Volara Type A, which is a crosslinked polyethylene foam. The product is manufactured and sold by Voltek, Ind., Lawrence, Mass. The expression "ethylene-containing polymer foam" used herein includes polyethylene homopolymer and ethylene-containing copolymers, preferably containing a major portion, by weight, of ethylene. It is preferred that the polymer present be crosslinked. Preferred comonomers, for preparing the polymers, include vinyl acetate, acrylic and methacrylic acids and esters, such as ethyl acrylate. Blends of such polymers can also be used. Preferably, the formulation is prepared in sheet form at approximately ⅛ inch thickness. The sheet is subjected to thermal molding at a temperature of bout 260° F. to form the foam shell.

The liquid-permeable facing 14 provided on the absorbent structure of the present invention is an apertured plastic film or a nonwoven fabric having a high degree of moisture permeability. For example, the nonwoven fabric may comprise polyester, polyethylene, polypropylene, bicomponent, nylon, rayon, or the like fibers. Preferably, a nonwoven fabric is used as cover 14. This nonwoven fabric has a basis weight in the range of 0.3 to 5.0 oz. per square yard and a density less than 0.2 gms/cc. Plastic films which are perforated or noncontinuous are also satisfactory. Though cover 14 is moisture permeable, it is preferably of the type which after permeation of the moisture, prevents strike-back of the body fluid. As indicated earlier, facing 14 is sealed to the outwardly extending flange 15 of shell 12 so as to enclose absorbent core 13 therein. In the preferred embodiment, cover 14 comprises a web of through air bonded bicomponent (polyester core/polyethylene sheath) fibers. Suitable results have been obtained using such a fabric of basis weight 0.5 oz/yd$^2$ and formed from 3d 1½" bicomponent staple fiber.

Absorbent medium 21 is substantially more wettable than facing 14 and transfer layer 23 and therefore tends to draw liquid away from these components. Since transfer layer 23 has very low resistance to liquid flow and as mentioned earlier, extends downwardly over the side edges of absorbent medium 21, it provides a liquid path into the bottom of shell 12 between the shell wall and absorbent medium 21. Such transferred liquid is held in the bottom of the pad 10 until absorbed by absorbent medium 21. Transferring discharged fluid to the bottom of pad 10 expedites fluid immobilization. Transfer layer 23, because of its M-folded configuration, high loft and ability to transfer discharged liquid, tends to keep the body of the user out of contact with said discharged liquid.

The disposable absorbent urinary pad 10 of the present invention is worn by the user in the crotch region, and for simplicity is secured to the underclothing of the wearer. Securement may be effected by the aforementioned adhesive lines or strips on the exterior of the shell, or the product may be secured to the underclothing by means of friction. If the product is to be secured by friction, a material for manufacturing the shell is selected which will provide sufficient friction or a material is coated on the exterior of the shell to provide such friction.

It will be understood that numerous variations and modifications may be effected without departing from the spirit and scope of the present invention.

What is claimed is:

1. In a disposable urinary pad having a body facing surface and a garment facing surface and comprising a liquid impermeable backing, a liquid-permeable facing, and a longitudinally extending absorbent core therebetween, the improvement wherein the absorbent core comprises:

an absorbent medium consisting essentially of a fibrous web exhibiting wet resilience, dry resilience, and liquid absorptive properties and, adjacent to one surface of said absorbent medium, a liquid permeable transfer layer, said transfer layer exhibiting high loft, resiliency and low resistance to liquid flow and low wettability relative to said absorbent media;

said absorbent core being further characterized by having a transverse cross-sectional configuration in the shape of a single letter M in the central area of the core, said shape resulting from a longitudinal channel being formed in the body facing surface of the core, wherein the transverse layer lines the channel and extends over the body facing surface and down the sides of the absorbent medium.

2. The urinary pad of claim 1 wherein said channel extends only in the central longitudinal portion of said absorbent core.

3. The urinary pad of claim 1 wherein said channel extends throughout substantially the entire longitudinal length of said absorbent core.

4. The urinary pad of claim 1 wherein the absorbent medium comprises hydrophobic fibers and super absorbent material.

5. The urinary pad of claim 1 wherein said backing is a substantially flexible, ethylene containing polymer foam shell.

6. The urinary pad of claim 5 wherein said foam shell has a thickness of about 1/64 inch to about ¼ inch.

7. The urinary pad of claim 1 wherein adhesive means are positioned on the garment facing surface of said liquid impermeable backing for temporary, but securely adhering said backing to the crotch portion of a nether garment.

8. The urinary pad according to claim 1 wherein said absorbent medium comprises about 50 to about 95% wood pulp and about 50 to about 5% non-cellulosic synthetic fibers.

9. The urinary pad of claim 8 wherein said absorbent medium comprises about 75 to about 85% by weight of wood pulp and about 20 to 25% by weight of non-cellulosic synthetic fibers.

10. The urinary pad according to claim 8 wherein said synthetic fibers are polyethylene fibers.

11. A urinary pad in accordance with claim 8 wherein said absorbent media comprises super absorbent, present in said absorbent medium in the amount of about 10 to about 50% by weight of the wood pulp plus the synthetic fibers.

12. A urinary pad according to claim 11 wherein said super absorbent is sodium acrylate.

13. A urinary pad according to claim 11 wherein said absorbent medium comprises a mixture of wood pulp, synthetic fibers and super absorbent which has been collected on to a layer of tissue and then thermally bonded.

14. A urinary pad according to claim 11 wherein said transfer layer comprises a high loft non-woven synthetic fiber fabric.

15. A urinary pad according to claim 14 wherein said fabric is a polyethylene fabric.

16. A urinary pad according to claim 1 wherein said liquid-permeable facing is selected from films and fabrics of polyester, polyethylene, polypropylene, bi-component fibers, nylon and rayon.

17. A urinary pad according to claim 16 wherein said liquid-permeable facing comprises a thermally bonded web of polyester/polyethylene bicomponent fiber.

* * * * *